United States Patent [19]

Bilger et al.

[11] Patent Number: 4,871,681
[45] Date of Patent: Oct. 3, 1989

[54] METHOD FOR THE COLORIMETRIC DETERMINATION OF THE CYANIDE CONCENTRATION OF AQUEOUS SOLUTIONS

[75] Inventors: Edgar Bilger, Hasselroth; Hubert Wolf, Hammersbach, both of Fed. Rep. of Germany

[73] Assignee: Degussa Aktiengesellschaft, Frankfurt am Main, Fed. Rep. of Germany

[21] Appl. No.: 126,095

[22] Filed: Nov. 30, 1987

[30] Foreign Application Priority Data

Dec. 3, 1986 [DE] Fed. Rep. of Germany ....... 3641251

[51] Int. Cl.$^4$ ............................................ G01N 21/78
[52] U.S. Cl. ...................... 436/109; 422/88; 422/86; 422/91; 436/164
[58] Field of Search ..................... 422/55–57, 422/86, 88, 90–92, 106; 436/58, 164, 169, 902, 905, 109; 423/236, 352

[56] References Cited

U.S. PATENT DOCUMENTS

4,299,593 11/1981 Dopp .................................. 436/109
4,321,059 3/1982 Voigt et al. ........................ 436/109

FOREIGN PATENT DOCUMENTS

2413546 10/1975 Fed. Rep. of Germany .
0052590 4/1979 Japan ................................... 436/109

OTHER PUBLICATIONS

"Determination of Nanogram Quantities of Simple and Complex Cyanides in Water", Goulden et al., Analytical Chem., vol. 44, No. 11, 9-1972, pp. 1845–1849.
Patents Abstracts of Japan, Metallic Ion Analyzer, No. 60-57,239, Nippon Kokan K.K. (Aug. 2, 1985).

*Primary Examiner*—Barry S. Richman
*Assistant Examiner*—T. J. Wallen
*Attorney, Agent, or Firm*—Beveridge, DeGrandi & Weilacher

[57] ABSTRACT

According to the invention, cyanide concentrations of approximately 0.001 to 5 mg cyanide/l are colorimetrically determined in a continuous manner by means of the known cyanidepicric acid color reaction. The solution containing free cyanide and/or cyanide releasable from cyanocomplexes is converted in a system enclosed in a gas-tight manner in the presence of chelate complexing agents, picric acid and alkaline buffer systems in 1–60 minutes at 50°–120° C. to the color complex and the absorbency is measured spectrophotometrically. The method avoids the extraction step which was previously necessary under 0.2 mg CN/l, avoids errors due to HCN gas evolution losses, is easy to manage, not prone to trouble and suitable for the continuous monitoring of waste-water streams or for controlling cyanide detoxification methods.

9 Claims, 1 Drawing Sheet

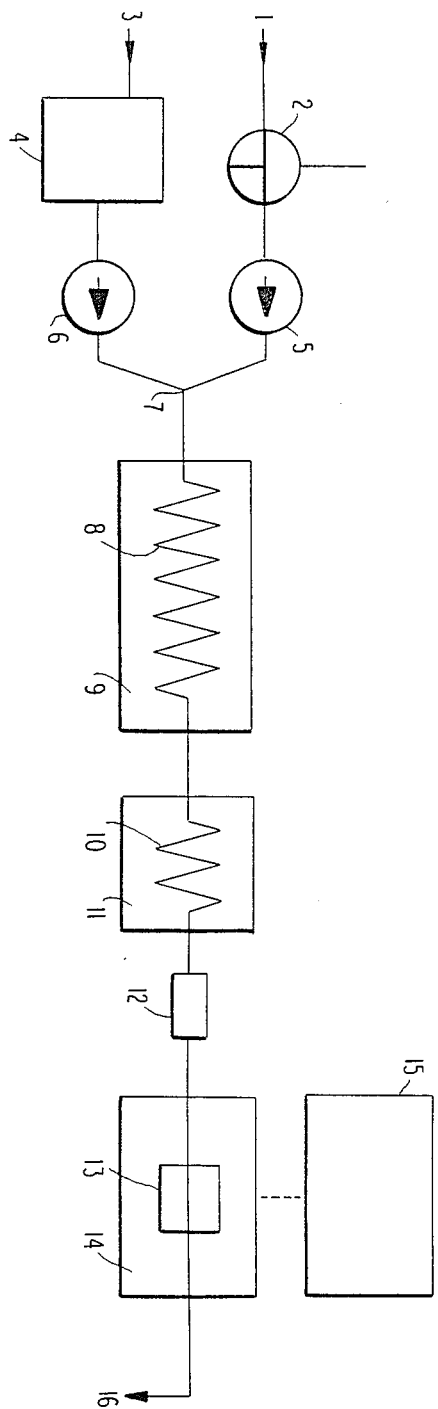

METHOD FOR THE COLORIMETRIC DETERMINATION OF THE CYANIDE CONCENTRATION OF AQUEOUS SOLUTIONS

The present invention relates to a method for the improved, especially continuous, colorimetric determination of the cyanide concentration of aqueous solutions, especially of waste water streams, whereby the color reaction is based on the reaction of cyanide ions with picric acid in an alkaline environment. Cyanide which can be released from cyanocomplexes in the presence of chelate complexing agents is also detected and cyanide concentrations in the range of approximately 0.001 to 5 mg CN/l are spectrophotometrically determined. The method can be performed in an easy and reliable manner and also permits the detection of cyanide concentrations in a concentration range under 0.2 mg CN/l without an extraction step Aqueous solutions, especially waste water streams, which contain free cyanides and cyanocomplexes, accumulate in amounts which can be very great in various industries, e.g. in processes for the hardening and the quenching and tempering of metals, in the treatment of ores by leeching and selective flotation, in the scrubbing of waste gas in blast furnace processes, in electroplatingtechnology and in the chemical industry.

Due to its high toxicity, such waste water can not be allowed to pass directly into bodies of water but rather it must be first detoxified. In order to achieve the cyanide limiting values prescribed or required by law for the introduction of waste water stream into the sewage system or into open bodies of water, which is in general 0.1 to 1.0 ppm, various methods are available. In addition to the long-known method for detoxification using hypochlorite, oxidative methods with environmentally safe hydrogen peroxide are increasingly used; moreover, other peroxigenated compounds and other oxidation chemicals are also being used for cyanide detoxification.

Regardless of the particular method used, each cyanide detoxification method requires a method of analysis specifically designed for it. One must in particular take into consideration whether and to what extent the particular method of analysis is affected and possibly disturbed by other substances present in the system, e.g. certain ions, reaction products resulting from the detoxification or by excess detoxification reagent. The skilled worker in the art has available, for example, argentometric, electrochemical and colorimetric methods of analysis for the discontinuous and partially continuous determination of the cyanide concentration. However, these methods can not be generally used, as has already been explained, because of possible disturbances and because of their differing measuring range.

Increasingly higher demands are being placed on methods for the continuous determination of the cyanide concentration of e.g. waste water streams. Such methods must make possible the reliable and continuous detection of the cyanide concentration under constantly changing operating conditions. They must assure the detection of even very slight concentrations around or below 0.1 mg CN/l in order to take into account the increasingly stringent requirements of the law. Such methods must also function smoothly even under difficult operating conditions, be simple to operate by personnel with little chemical and analytical training and be able to be performed with low maintenance costs. In addition, it is especially important that other substances present in the waste water, e.g., cyanate ions or phenols and the detoxification agent, e.g. hydrogen peroxide, should not cause any problems.

A continuous electrochemical method for the determination of the cyanide concentration by means of potentiostatic apparatus is known, cf. DECHEMA monograph No. 75; 1974, pp. 295–309. This method does permit the measurement of slight concentrations of cyanide, but can be used in practice only in a very limited manner since the most important condition, namely, the absence of strongly reducing and oxidizing substances, is very often not present. For example, hydrogen peroxide causes problems; the precipitation of the very troublesome sulfide as lead sulfide was not satisfactory in practice.

The known barbituric acid-pyridine method for the colorimetric determination of the cyanide concentration is based on the formation of a polymethine dye, cf. E. Asmus and H. Garschagen in "Zeitschrift for Analytische Chemie", vol. 138, pp. 414–422; 1953.

This method has also previously been used for the continuous colorimetric determination of cyanide. However, it exhibits a few serious disadvantages which limits its applicability. Thus, for example, reduction agents, rhodanide, sulfite, sulfide, cyanate and hexacyanoferrate ions as well as hydrogen peroxide cause problems. These disturbances can be avoided in the discontinuous determination by freeing the hydrogen cyanide from the cyanides, transferring it into a receiving flask with sodium hydroxide solution and determining it there. It is clear that this method can not be used in a continuous determination. Other disadvantages are the chronologically very limited ageing resistance of the chloramine T- and pyridine-barbituric acid reagent solution required for the color formation and the fact that cyanides of certain metals such as e.g. nickel, copper silver and gold can not be detected or can be detected only to a very limited extent.

The long-known isopurpurate reaction of picric acid for the qualitative and quantitative determination of cyanide ions has been investigated very extensively, cf., for example, F. B. Fischer and J. S. Brown in "Analytical Chemistry", vol. 24, 1952, No. 9, pp. 1440–1444. The method improved by D. J. Barkley and J. C. Ingles, which made it possible to also detect cyanide freed from cyanocomplexes in addiction to free cyanide, can be employed for the discontinuous colorimetric determination of cyanide, cf. "Research Report R 221", Department of Energy, Mines and Resources, Mines Branch, Ottawa, February 1970. The formation of the cyanide-picric acid color complex is generally not interfered with or is only interfered with in the presence of very high concentrations by means of substances such as hydrogen peroxide, phenols, cyanate, rhodanide, thiosulfate and sulfite ions, in contrast to the barbituric acid-pyridine method.

However, a problem of the discontinuous cyanide-picric acid method which was not recognized at first developed wherein hydrogen cyanide gas evolution losses can not be completely avoided and therewith too low values of cyanide concentration are found. The deviations from the theoretical value are generally greater in the determination of free cyanide than in the case of cyanide which can be freed from cyanocomplexes.

Barkley and Ingles, supra, supply no indications of how to perform the discontinuous method continuously. This was also not obvious, because for the determination of concentrations under 0.2 ppm, the color complex formed first in aqueous phase had to be extracted before the absorbency measurement in a further method step with chloroform in the presence of a quaternary ammonium salt and the time involved for a single determination was approximately one hour. The necessity of having to use an organic solvent as well as the considerable time required and the expense for the equipment did not result in a simple continuous determination which could be performed with low maintenance cost for the equipment.

SUMMARY OF THE INVENTION

The present invention has the object of creating an improved method based on the known colorimetric cyanide-picric acid color reaction which permits the determination of the cyanide concentration of aqueous solutions in a range of approximately 0.001 to 5 mg cyanide per liter in a simple and reliable manner. The invention has the advantage of avoiding the possibility of error due to HCN gas evolution and eliminating of the use of an organic solvent and the extraction step.

BRIEF DESCRIPTION OF THE DRAWING

The accompanying drawing is a schematic flow diagram illustrating the method of the invention.

DETAILED DESCRIPTION OF THE INVENTION

The present invention provides a method for the improved colorimetric determination of the cyanide concentration in the range of approximately 0.001 to 5 mg/l of aqueous solutions containing free cyanide and/or cyanide which can be freed in the presence of chelate complexing agents from cyanocomplexes, whereby an extraction step is eliminated for the determination of the cyanide concentration under 0.2 ppm. The determination reaction is carried out by means of reacting the free cyanide and the cyanide which can be freed in the presence of chelate complexing agents from cyanide complexes with picric acid in an aqueous alkaline environment with heating, subsequently cooling of the solution containing the red cyanide-picrate color complex formed and spectrophotometrically measuring the absorbency of this solution at approximately 520 nm. The absorbency of a blank test free of cyanide is taken into consideration. It is a feature of the invention that in a system enclosed in a gas-tight manner the test solution is brought into contact with the chemicals required for color formation, cyanide release and pH adjustment and the reaction to the cyanide-picrate color complex, which occurs in the presence of acid-base pairs which buffer the pH, is carried out.

It is a further feature of the invention to carry out the method in a continuous manner.

It was surprisingly found that the cyanide concentration of aqueous solutions which contain free cyanide and/or cyanide which can be released in the presence of chelate complexing agents from cyanocomplexes can be determined very precisely and in a reliably reproducible manner if both the test solution is brought into contact with the alkaline picric acid reagent solution and also the conversion to the cyanide-picrate color complex is performed in a system enclosed in a gas-tight manner such as can be easily created, for example, in the equipment described. A system enclosed in a gas-tight manner signifies one that contains only a liquid phase, that is, practically no gaseous phase is present in the system. Under this condition, the same absorbency values are obtained at the same cyanide concentration in the spectrophotometric measurement of absorbency, regardless of whether the test solution contains free cyanide, e.g. Na CN, or cyanocomplexes, e.g. Na [Ag $(CN)_2$] or $Na_2$[Ni $(CN)_4$] or a mixture of both—cf. the non-enclosed system of example 1 with the system enclosed in a gas-tight manner according to example 2. Moreover, the absorbency values recorded as a function of the concentration in the determination in the enclosed system are located on a straight line.

The advantageous effects surprisingly achieved by the system enclosed in a gas-tight manner are essential conditions for a continuous method of determining the cyanide concentration of aqueous solutions with optionally rapidly changing concentration and regarding the type of cyanocompound of changing composition.

It was also found that in the determination of the cyanide concentration in a gas-tight system in accordance with the invention, not only cyanide concentrations in a range between 0.2 and a few mg CN/l can be reliably detected directly, that is, without an additional extraction step or any other preconcentration of the colored solution, by means of the absorbency measurement of the cyanide-picrate color complex formed in aqueous phase, but also such concentrations which are located in a range of approximately 0.001 to 0.2 mg cyanide per liter. The total measuring range which can be detected by the method of the invention ranges from about 0.001 to 5 mg cyanide per liter aqueous solution; 0.01 to 3 mg/l can be detected especially well. The achievable lower limit value depends optionally on the spectrophotometer used. The detection of very slight concentrations, especially those under 0.01 mg CN/l, generally requires the usage of a device which a very good measuring amplifier and turbidity compensation device. In general, the error in the concentration range below 0.01 mg CN/l is greater than it is in the range thereabove.

It is possible to determine cyanide concentrations over 5 mg/l with the method of the invention, however, in order to obtain precise measuring values, it is recommended that the test solution be diluted in such a manner before, during or after dosing into the equipment in accordance with the invention that a cyanide concentration of 3 mg/l is not exceeded in the solution mixture.

In general, the chemicals required for color formation, cyanide release and pH adjustment and buffering are added in the form of one or several aqueous solutions to the solution to be determined. It is especially preferable to use an alkaline picric acid reagent solution containing all the required chemicals. A person skilled in the art should check first with simple tests whether the selected chelate complexing agents, bases and buffer combinations are compatible with the picric acid and yield a solution stable in storage. The specific materials are well known in the art for this purpose.

The dosing of the test solution and reagent solution or solutions is advantageously performed by means of precisely controllable dosing pumps into a mixing zone which can be designed e.g. as a simple section of pipe or as a section of pipe provided with static mixing devices. From the mixing zone, the solution mixture passes for the formation of the color complex into a heatable tubular flow reactor. This tubular flow reactor preferably exhibits a slight inner diameter and is generally positioned spirally in a unit heater. This apparatus is known in the art. For the formation of the color, the solution mixture is pumped through the reactor, whereby the mixture is heated 1 to 60 minutes to 50° to 120° C., preferably 5 to 20 minutes to 80° to 110° C. The required dwell time at a given temperature is a function both of the composition of the reagent solution as well as of the cyanocomplexes which may be contained in the test solution from which complexes cyanide is released at different rates in the presence of chelate complexing agents. Thus, in the lower temperature range a longer reaction time is required than in the upper temperature range. The flow rate in the tubular flow reactor is to be set so that no significant remixing occurs in the reactor during the dwell time.

According to the method of the invention using the tubular flow reactor, the solution mixture is brought within a very short time to the desired reaction temperature. The color formation can also be performed at temperatures between the boiling point of water and 120° C. if care is taken that the appropriate back pressure is built up by a device, e.g. a throttle valve, preferably located after the flow cooler and therefore the formation of gas bubbles is avoided. Both features are suitable for holding the reaction time as low as possible, which is particularly significant if the continuous determination of cyanide concentration is used to control a continuous cyanide detoxification or for the final checking of waste water, or if the test solution contains cyanocomplexes, e.g., $Ag(CN)_2^-$, from which the cyanide can be released less readily. While a quantitative detection of cyanide bound in $Ag(CN)_2^-$ was often not possible or possible only after a very long reaction time at boiling temperature according to the known discontinuous method, it can be performed without difficulty according to the method of the present invention.

Cyanide which can be detected in accordance with the invention denotes cyanide present in dissociated form in aqueous solution. Cyanide which can be released from cyanocomplexes denotes in particular cyanide which is released from cyanocomplexes of zinc, cadmium, copper, nickel and silver in the presence of chelate complexing agents and is made accessible therewith to the formation of color. Cyanoaurates release cyanide under the usual reaction conditions by means of recomplexing with DTPA usually only incompletely. On the other hand, cyanocomplexes of cobalt and of iron release cyanide not at all or only to a slight extent.

Chelate complexing agents, especially chelate complexing agents with a functionality of four and higher, are used for recomplexing cyanocomplexes. The chelating agents can contain e.g. as functional groups per molecule either hydroxyl and carboxyl groups, several amino groups or amino and carboxyl groups or amino and phosphonate groups. The following can be used, for example: tartaric acid, diethylene triamine, nitrolotriacetic acid; however, it is preferable to use stronger chelate complexing agents such as ethylene diamine tetraacetic acid (EDTA) or diethylene triamine pentaacetic acid (DTPA) or ethylene diamine tetrakis(methylene phosphonate) or their water-soluble salts, e.g. alkali salts.

The formation of color to the cyanide-picrate color complex is a function of the pH as regards its rate of formation and its color intensity. The conversion is usually performed in aqueous alkaline environment, whereby, however, a pH in the range of approximately 7.1–12 is preferable and a pH of approximately 9±0.5 is especially preferable.

In order to obtain reliably reproducible results of the determination of the cyanide concentration, even in the case of a rapidly changing cyanide content and pH and of a different composition of the aqueous test solution, it is necessary to perform the conversion to the color complex in the presence of one or several acid-base pairs which buffer the pH. When selecting and determining the amount of the acid-base pairs, the person skilled in the art must bear in mind that it is desired to obtain the desired pH with a broad buffer level adjusted to the particular application and sufficient buffer capacity.

For adjusting the pH, alkali hydroxides and/or alkali carbonates and/or other compounds acting in an alkaline manner can be used in particular. Especially suitable acid-base pairs for buffering are buffers based on borax and sodium hydroxide. Chelate complexing agents such as e.g. EDTA or DTPA also act in the presence of their alkali salts as buffering acid-base pairs.

It is especially advantageous to compound the test solution containing cyanides continuously with such an amount of an alkalinely buffered picric acid reagent solution containing chelate complexing agents so that the solution mixture exhibits a pH between 8.5 and 9.5 and contains approximately 0.001 to 3 mg free and/or releasable cyanide per liter and whereby 0.5 to 3.0 g picric acid, 2 to 20 g EDTA or DTPA, 1 to 10 g NaOH and 1 to 10 g $Na_2B_4O_7$ are used per liter.

In general, the solution mixture leaving the flow reactor is cooled down, e.g. in a flow cooler, to the temperature at which the absorbency measurement is performed. Usually, the solution mixture is cooled down to 15° to 30° C. and is allowed to flow at this temperature, generally after a release of pressure to normal pressure, through the flow cuvette of a spectrophotometer.

Single-beam or double-beam spectrophotometers which are preferably provided with a device for turbidity compensation, which largely prevents a disturbance due to suspended substances causing turbidity, can be used for measuring the absorbency. It is advantageous to connect the output of the continuously operating photometer to a continuous-line recorder in order to record the measured values.

The adjustment to the zero point by means of a cyanide-free blank test, the setting up of a calibration curve by means of calibrating solutions and the measuring of the absorbency of the test solutions can be carried out in a known manner. For purposes of monitoring, a switching is performed at intervals from the test solution to the blank test or, optionally, also to the calibrating solutions, which are treated in accordance with the invention. The layer thickness of the flow cuvette is generally 1 to 8 cm. The measuring is performed at a wavelength between 510 and 530 mm, preferably at 520 mm.

The technical advance of the method of the invention resides in that it is now possible for the first time to utilize the cyanide-picrate color reaction for the continuous determination of concentration and therewith to employ this method for the continuous monitoring of streaming of waste water or for controlling cyanide detoxification methods. Moreover, such slight concentrations of cyanide can also be directly determined in a simple manner with the invention for which an additional step was required in the known discontinuous method, namely, an extraction with an organic solvent. In addition, considerable advantages over the known discontinuous method are the reliably reproducible detectibility of the cyanide concentration regardless of its absolute level and presence as free and/or releasable cyanide, the low manual expense for operating and servicing the measuring equipment and the low cost for chemicals—practically any desired amount of measuring data can now be detected during a determined operating period with the amount which was previously required for a single determination.

The continuous determination of the cyanide concentration in accordance with the method of the present invention can be performed in an especially adavantageous manner in an apparatus according to the drawing. The apparatus comprises devices 5,6 for the continuous dosing of the test solution 1 containing cyanide or several aqueous solutions 3 containing one or more chemicals for color formation, cyanide release and pH adjustment, devices 7 for bringing together and mixing these solutions, a tubular flow reactor 8 provided with heating devices 9 for heating to 50° to 120° C., a tubular flow cooler 10 provided with cooling devices 11 for cooling down to 10° C. the solution leaving the reactor, followed by devices 12 for regulating the pressure and a spectrophotometer 14, advantageously connected to a continuous line recorder 15 for continuously recording the absorbency. The apparatus functions to carry the solution mixture form a system enclosed in a gas-tight manner between dosing points 5,6 and the regulating of pressure 12. In the figure, reference numeral 4 signifies a supply vessel for the picric acid reagent solution containing all chemicals, 16 is the run-off and 13 the flow cuvette of spectrophotometer 14, 2 is a three-way valve for switching from the test solution to the blank solution/calibrating solution.

As already mentioned, it is essential for the invention that practically no gaseous phase forms when the solutions are brought together and converted at elevated temperature to the color complex. This is for the reason that gaseous phase could distort the results. No significant remixing occurs inside the equipment. This is taken into account when the equipment is designed by positioning the devices in the sequence previously indicated and by designing the parts which carry the solution mixture to be pressure-resistant, corresponding at least to the water vapor pressure of the maximum temperature of the flow reactor.

Tubular flow reactor 8 with a small inner diameter advantageously comprises a volume of 10 to 150 ml and a diameter of 1 to 5 mm. The flow reactor is arranged in accordance with the heating unit: Flow reactor 8 is advantageously positioned in a spiral manner in order to house it in a small area, e.g. in a heater unit 9 which can be a solid-bed heater unit or a liquid-bed heater unit (thermoblock).

It is advantageous if the design of coolable flow cooler 10,11 resembles that of the reactor, whereby a volume of 1 to 15 ml generally meets the cooling requirements.

Known pressure regulating devices 12, preferably a throttle valve, are used to build up a pressure in the reaction part of the equipment and for relieving the pressure of the solution mixture cooled down to absorbency-measuring temperature. Any sensitive single-beam or double-beam spectrophotometer can be used, preferably a spectrophotometer with turbidity compensation.

The equipment used by way of example makes it possible to continuously perform the result of cyanide detoxification while avoiding the time-consuming analysis for "readily releasable cyanide" according to DIN 38 405 D 13.2. The equipment is characterized by a simple design, simple manner of operation, high degree of accuracy and good ability to detect in a concentration range between approximately 0.001 to 5 mg cyanide per liter and can be employed in many areas of the chemical industry and of mining technology.

EXAMPLE 1

(State of the Art)

Discontinuous determination of cyanide

For measuring the absorbency of free cyanide being derived from NaCN and of cyanide which can be released from $Na_2[Ni(CN)_4]$ in the presence of diethylene triamine pentaacetic acid (DTPS), aliquot amounts with 25, 50, 100, 150 and 200 μg cyanide were taken from previously prepared standard solutions of NaCN and of $Na_2[Ni(CN)_4]$, transferred into 100 ml Erlenmeyer flasks and brought to the same volume of 70 ml. 25 ml of the buffered alkaline picric acid reagent solution containing DTPA was added to each of them as well as to a blank test. The reagent solution was prepared by dissolving 6 g picric acid, 40 g DTPA, 16 g NaOH in approximately 800 ml water, adding 14 g $Na_2B_4O_7$ and 14 g $Na_2CO_3$ and filling to 1000 ml. The specimens compounded with the reagent solution were heated 30 minutes on a boiling water bath, cooled down to 25° C., transferred into 100 ml measuring flasks and brought to volume. The absorbency in comparison to the blank test was measured in a single-beam spectrophotometer at 520 mm in a customary manner using cuvettes with a layer thickness of 1 cm. As the results of the following table show, the absorbency values are not located on a straight line which is valid in this range, as was determined by a dilution series. The measured values of the specimens containing the cyanocomplex are located above those of the specimens containing the corresponding amount of free cyanide.

| | extinction | |
| μg CN/specimen | NaCN | $Na_2 Ni(CN)_4$ |
| --- | --- | --- |
| 25 | 0.053 | 0.055 |
| 50 | 0.104 | (0.127) |
| 100 | 0.205 | 0.210 |
| 150 | 0.294 | 0.314 |
| 200 | 0.385 | 0.404 |

EXAMPLE 2

Continuous determination of the cyanide concentration

The equipment used included a dosing container for the picric acid reagent solution, same composition as in example 1, an input for the test solution or calibrating solution which can be switched via a three-way magnet valve, a dosing pump for the reagent solution and one for the test solution, a tubular flow reactor of V4A steel cast in a spiral fashion in a solid-bed thermoblock which reactor exhibited a volume of 150 ml and an inner diameter of 5 mm, of a flow cooler with a volume of 25 ml designed in the same manner and cast in a cooling block, a throttle valve and of a single-beam spectrophotometer with turbidity compensation whose output was connected to a continuous line recorder.

Test solutions containing NaCN and $Na[Ag(CN)_2]$ with 1.82 mg, 0.73 mg, 0.36 mg and 0.07 mg free and releasable cyanide per liter solution were prepared.

For calibration first water and reagent solution were brought together in a ratio of 3:1 by the dosing pumps, mixed in a pipe section reaction functioning as mixer and conducted after passing the thermoblock (heating unit) heated to 100° C., cooling down to 25° C. and pressure release to the spectrophotometer for adjustment of the zero point; 8 cm cuvette, measuring wavelength 520 n.

The straight through flow of the solution mixture was 1.2 l/hr, the dwell time between dosing and measuring 17 minutes. After the three-way magnet valve had been switched to the solution to be determined, the test solutions were dosed in while retaining the other conditions one after the other, each during a time period of 5 minutes. The measured values follow from the table and show that free $CN^-$ and cyanide releasable from $Ag(CN)_2^-$ and mixtures of both are detected in the same manner and all measured values are located on a straight line with only slight dispersion.

| mg $CN^-$/l (free and releasable cyanide) | extinction | |
|---|---|---|
| | NaCN | $Na[Ag(CN)_2]$ |
| 1.82 | 0.302 | 0.306 |
| 0.73 | 0.121 | 0.121 |
| 0.36 | 0.061 | 0.062 |
| 0.07 | 0.013 | 0.013 |
| 0.36° | 0.062 | |
| 0.07° | 0.012 | |

°1:1 mixture of the solutions of the same concentration containing NaCN and $Na[Ag(CN)_2]$

EXAMPLE 3

Discontinuous determination-influence of buffering the reagent solution

According to example 1, 80 μg cyanide as specimens containing NaCN and $Na_2[Ni(CN)_4]$ were compounded with 25 ml each of the following reagent solutions and the absorbency of the cyanide-picrate complex measured after color formation.

| reagent solution | extinction | |
|---|---|---|
| | 80 μg $CN^-$ as NaCN | 80 μg $CN^-$ as $Ni(CN)_4$ |
| (a)° | 0.122 | 0.148 |
| (b)° | 0.163 | 0.169 |

°(a) = 6 g picric acid + 40 g DTPA + 16 g NaOH per l reagent solution
°(b) = like (a), but with 14 g $Na_2B_4O_7$ in addition.

Further variations and modifications of the foregoing will be apparent from the above to persons skilled in the art and are intended to be encompassed by the claims appended hereto.

German priority document No. P 36 41 251.1 is relied on and incorporated by reference.

We claim:

1. A process for colorimetrically determining the cyanide concentration of aqueous solutions in the range from 0.001 to 5 mg/liter, of free cyanide and cyanide released by chelating complexing agents from cyanocomplexes comprising:
   (a) continuously combining the aqueous solution to be tested with picric acid, with a chelating complexing agent and with chemicals to adjust the pH while retaining an aqueous, alkaline solution of reaction,
   (b) heating the solution of reaction to 50° to 120° C. while forming a red cyanide-picrate color complex,
   (c) cooling the reaction solution containing the red color complex, and
   (d) spectrophotometrically measuring the absorbency of the cooled reaction solution at a wave length approximately 520 nm with comparison to a cyanide-free blank sample and ascertaining by means of a calibration curve the cyanide concentration associated with said absorbency.
   where the combination of (a) and the heating of (b) take place in a closed, gas-tight system wherein the formation of a gas phase is avoided by means of back pressure.

2. The process according to claim 1, wherein the chemicals for adjusting the pH are acid-base pairs which buffer the pH value.

3. The method according to claim 2 wherein a buffer of borax and sodium hydroxide is used.

4. The process according to claim 1, wherein picric acid, chelating complexing agents and chemicals to adjust the pH value in the form of one or more aqueous solutions are combined continuously with the aqueous solution to be determined.

5. The process according to claim 4, wherein the temperature is raised to 80° to 110° C. for the reaction.

6. The process according to claim 1, wherein the chelating complexing agents have a functionality of four or higher.

7. The process according to claim 6, wherein the chelating complexing agents are selected from the group consisting of ethylene diamine tetraacetic acid, diethylene triamine pentacetic acid and the water-soluble salts thereof.

8. The method according to claim 1 wherein the reaction is performed at a pH in a range of about 7.1 to 12.

9. The method according to claim 8 wherein the pH is about approximately 9±0.5.

* * * * *